(12) United States Patent  
Barth

(10) Patent No.: US 8,313,236 B2  
(45) Date of Patent: Nov. 20, 2012

(54) THERMAL CONDUCTIVITY DETECTOR

(75) Inventor: Phillip W. Barth, Portola Valley, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 571 days.

(21) Appl. No.: 12/613,670

(22) Filed: Nov. 6, 2009

(65) Prior Publication Data

US 2011/0107816 A1    May 12, 2011

(51) Int. Cl.
*G01N 25/00* (2006.01)
(52) U.S. Cl. .................. 374/44; 374/43; 374/10
(58) Field of Classification Search ............ 374/43, 374/44, 41, 10, 11, 141, 185
See application file for complete search history.

(56) References Cited

U.S. PATENT DOCUMENTS

| | | | | |
|---|---|---|---|---|
| 4,057,755 A * | 11/1977 | Piesche | | 374/173 |
| 5,295,389 A * | 3/1994 | Nagata et al. | | 374/135 |
| 6,502,983 B2 * | 1/2003 | Yu | | 374/44 |
| 6,550,961 B1 * | 4/2003 | Ueda | | 374/44 |
| 6,896,406 B2 * | 5/2005 | Gellert | | 374/44 |
| 6,991,366 B2 * | 1/2006 | Naka et al. | | 374/44 |
| 7,038,209 B2 * | 5/2006 | Opfermann et al. | | 374/44 |
| 7,182,510 B2 * | 2/2007 | Cahill | | 374/44 |
| 7,753,582 B2 * | 7/2010 | Lopez et al. | | 374/44 |
| 7,951,144 B2 * | 5/2011 | Mahajan et al. | | 374/44 |
| 8,156,632 B2 * | 4/2012 | Mahajan et al. | | 374/44 |
| 2001/0012313 A1 * | 8/2001 | Yu | | 374/44 |
| 2004/0136435 A1 * | 7/2004 | Gellert | | 374/44 |
| 2004/0250601 A1 * | 12/2004 | Lin | | 374/44 |
| 2006/0222043 A1 * | 10/2006 | Cahill | | 374/44 |
| 2011/0107816 A1 * | 5/2011 | Barth | | 73/25.03 |

* cited by examiner

*Primary Examiner* — Yaritza Guadalupe-McCall

(57) ABSTRACT

A thermal conductivity detector includes a structure defining a cavity, the structure principally comprising a material having a first coefficient of thermal expansion; a sensing element for sensing a thermal conductivity of a gas flowing within the cavity, the sensing element having a second coefficient of thermal expansion different from the third first coefficient of thermal expansion, the sensing element being disposed at least in part within the cavity; and a compensation structure having a third coefficient of thermal expansion different from the first and second thermal coefficients of expansion. Over a selected temperature range, a stress within the sensing element is less than a yield stress of any component of the sensing element, and a stress within the compensation structure is less than a yield stress of any component of the compensation structure.

20 Claims, 8 Drawing Sheets

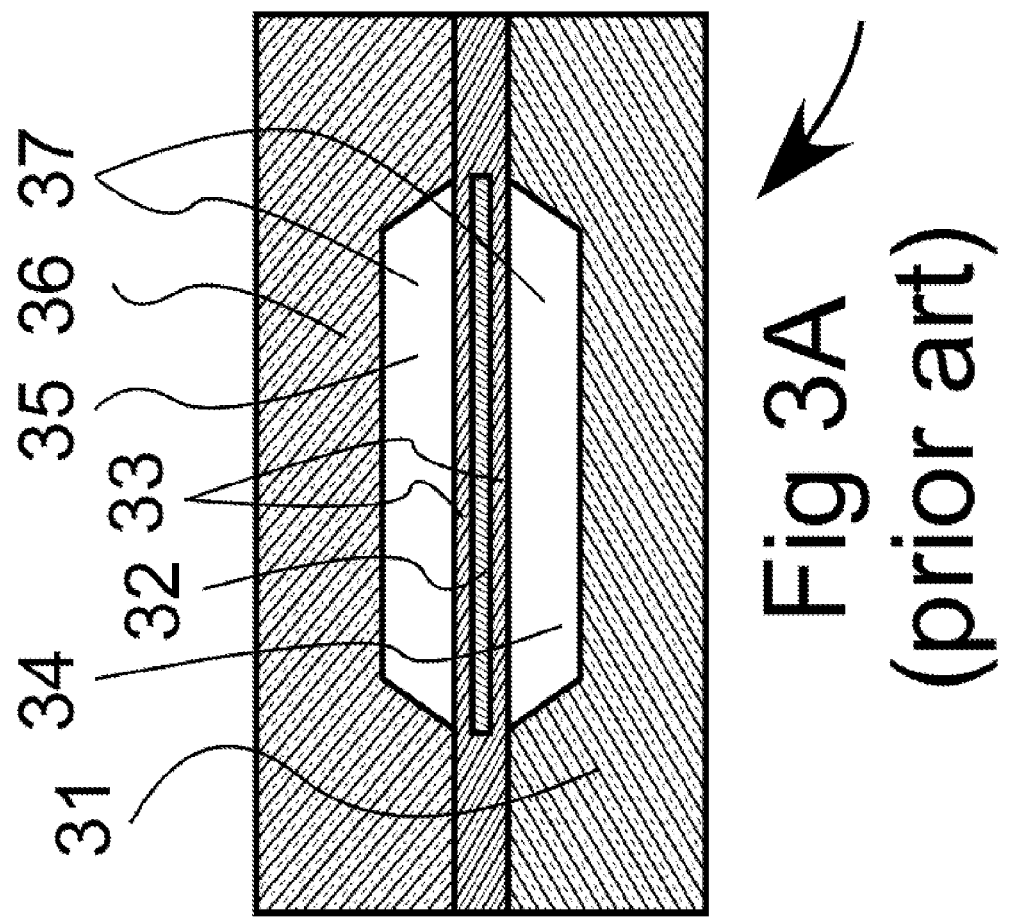

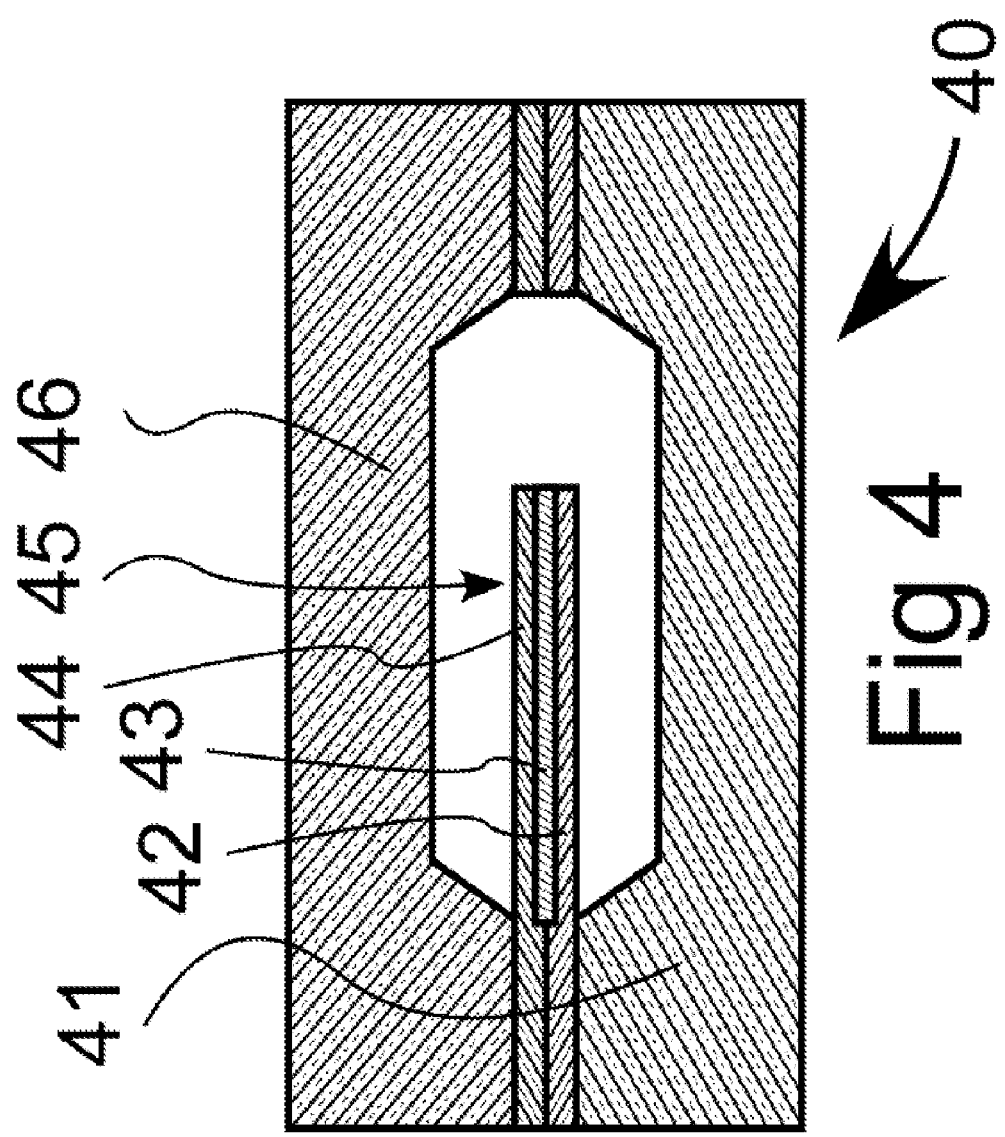

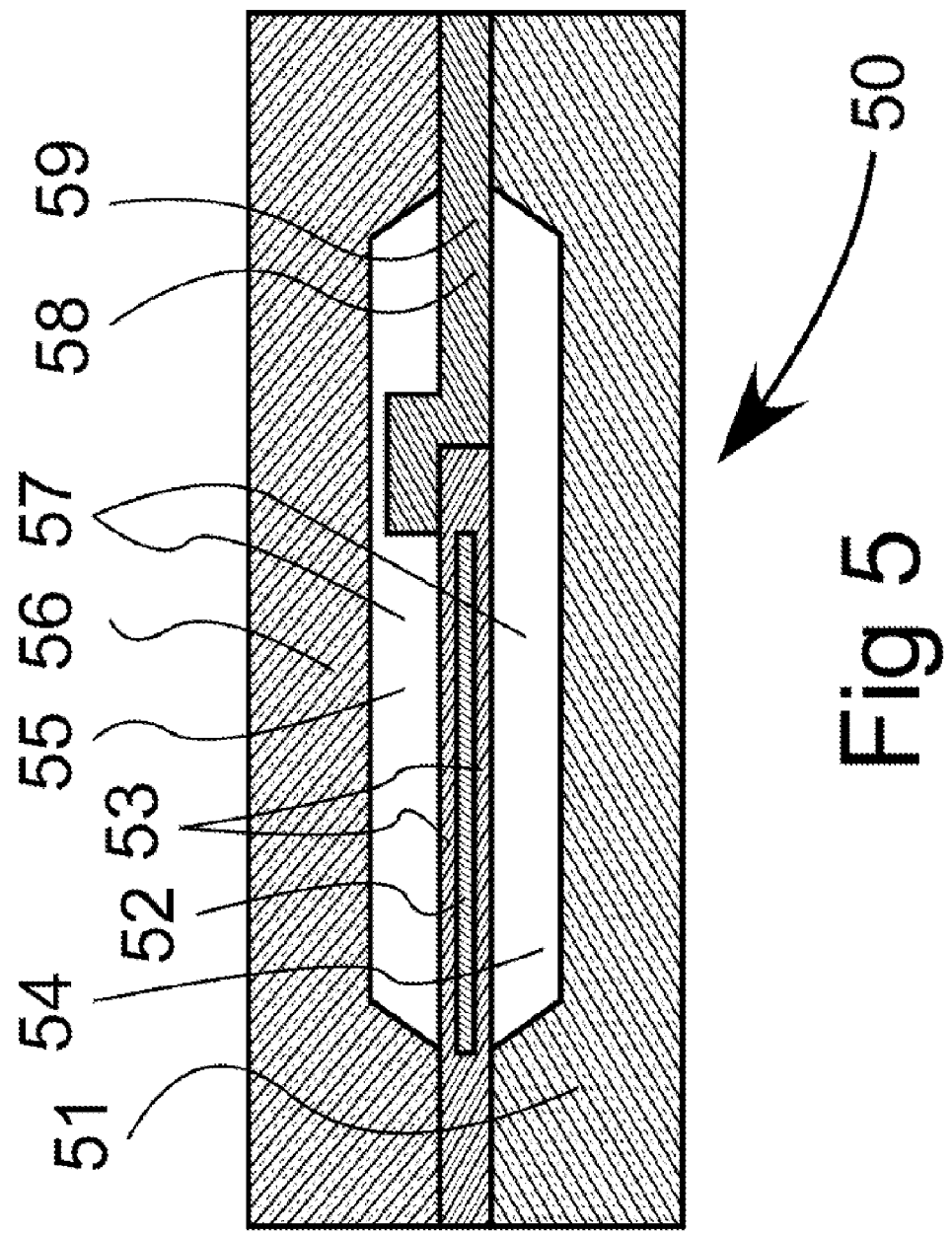

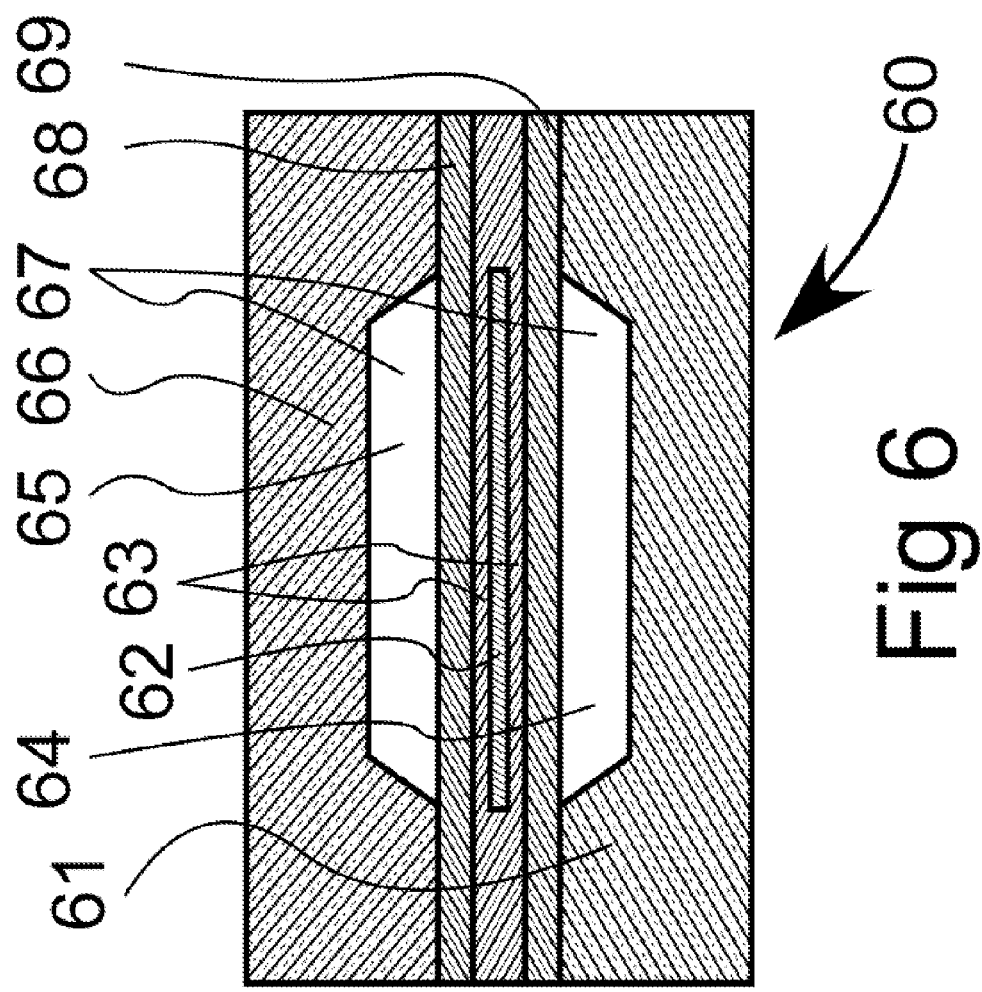

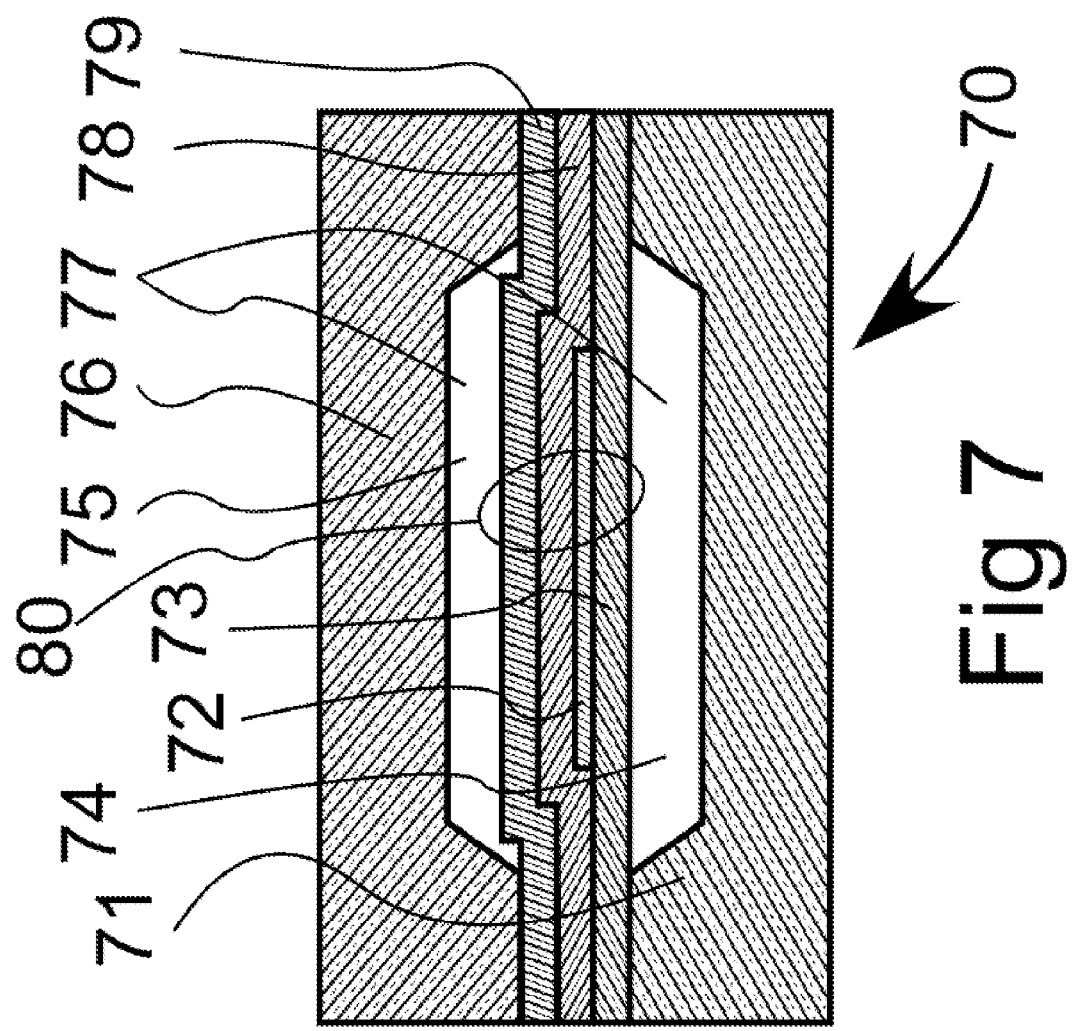

THERMAL CONDUCTIVITY DETECTOR

BACKGROUND

A thermal conductivity detector (TCD) may be employed in chromatography to detect components present in a sample gas. The device is particularly useful when placed at the output of a gas chromatograph (GC) where it can detect chemically distinct pulses of gas, called peaks, emerging at different times from the GC. In such an application, a TCD senses changes in the thermal conductivity of a column effluent comprising a sample gas which can be compared to a reference flow of a carrier gas, for example, helium. Since all compounds, organic and inorganic, have a thermal conductivity different from helium, all compounds can be detected by a TCD.

In general, a TCD consists of a thin electrically resistive filament in a temperature-controlled cell through which a gas (e.g., a column effluent) passes. In practice, a TCD monitors the thermal conductivity of the gas surrounding the thin electrically resistive filament by measuring the electrical power required to heat that filament to a given temperature. Gases with lower thermal conductivity require less power to heat the filament to a given temperature than gases with higher thermal conductivity. When an analyte elutes in a GC the thermal conductivity of the column effluent is reduced. In this case, if the column effluent is provided to the TCD, if the electrical power is kept constant then the filament heats up to a higher temperature and changes resistance. This resistance change may be sensed, for example, by a Wheatstone bridge circuit which produces a measurable voltage change.

FIG. 1 illustrates a Wheatstone bridge 10 employing TCDs 15a and 15b which can be employed in a gas chromatography system. A column effluent of a sample gas flows over resistor R3 in TCD 15a while a reference gas (e.g., helium) is passed over a second resistor R4 in TCD 15b in the four-resistor circuit. The reference gas flowing across resistor R4 of the circuit compensates for drift due to flow or temperature fluctuations. Changes in the thermal conductivity of the column effluent flow across resistor R3 will result in a temperature change of the resistor R3 and therefore a resistance change which can be measured as a signal. A described above, this temperature change will depend upon the gaseous compound currently flowing past the resistor, allowing that compound to be detected.

Two streams of development work have resulted in two different types of TCDs.

FIG. 2 illustrates a first type of prior art miniature thermal conductivity detector (TCD) 20, sometimes also referred to as a katharometer. TCD 20 includes a thin wire or filament 21 (e.g., tungsten or platinum), fixed on thicker metal posts 22 at two ends, the posts passing through electrical insulators 23 comprising, for example, glass. Wire 21 is suspended in a channel or cavity 24 formed in a substrate 25. A flowing gas whose properties are to be monitored is passed through channel 24, and filament 21 is employed as an electrically resistive filament analogous to a light bulb filament. If the gas medium surrounding wire 21 is mostly an inert medium such as helium, then filament 21 can be taken to a high temperature, for example 500° C., without burning out filament 21.

When filament 21 is at for example 500° C., substrate 25, for example comprising stainless steel, might typically be at 400° C. Typically, substrate 25 will have a higher coefficient of thermal expansion (CTE) than filament 21, and so filament 21 remains stretched taut even though it is at a higher temperature than substrate 25. If filament 21 failed to remain taut it could mechanically buckle, coming closer to the walls of channel 24, and its use as a detector would suffer. Of course if filament 21 were to stretch so tightly that it broke, then TCD 20 would become useless. Thus designing TCD 20 requires a balancing act between two CTEs, that of filament 21 and that of substrate 25.

Miniature TCDs such as TCD 20 have been successful, having utility over a high temperature range, so that they can characterize gases containing, for example, petroleum products that are liquid below 400° C. but gaseous at 400° C.

However, miniature TCDs require fairly large gas flow on the order of 20-50 standard cubic centimeters per minute (sccm) in order to give good accuracy. This high flow requirement is not well suited to the small-diameter capillary columns used in gas chromatography where the flow rates are on the order of 1-5 sccm. These low flow rates save gas and their use is desirable.

In order to take advantage of the existence of small-diameter capillary columns, a second stream of development produced microscale TCDs.

FIG. 3A illustrates one embodiment of a microscale TCD. TCD 30 includes: a first substrate 31; a filament 32; an electrically insulating film 33, and a second substrate 36. First and second substrates 31 and 36 together form a principle structure of TCD 30, and together define a cavity 37 in which filament 32 is, at least in part, disposed, and through which the sample gas whose properties are to be monitored can flow. Cavity 37 includes first and second troughs 34 and 35 with filament 32 suspended therebetween such that a column effluent comprising a sample gas flows around it, thereby allowing TCD 30 to detect the thermal conductivity of the gas.

However while microscale TCDs such as TCD 30 have been successfully employed at low temperatures, they have generally been unsuccessful at high temperatures. There are several reasons for this lack of success, among them being inadequate mechanical stability over a wide temperature range.

What is needed, therefore, is a microscale TCD providing both utility at low flow rates and mechanical stability over a wide temperature range.

SUMMARY

In an example embodiment, a thermal conductivity detector comprises: a structure defining a cavity, the structure principally comprising a material having a first coefficient of thermal expansion; a sensing element for sensing a thermal conductivity of a gas flowing within the cavity, the sensing element having a second coefficient of thermal expansion different from the first coefficient of thermal expansion, the sensing element being disposed at least in part within the cavity; a first insulating material substantially covering the sensing element, the first insulating material having a third coefficient of thermal expansion different from the first and second thermal coefficients of expansion; and a second insulating material substantially covering the first insulating material, the second insulating material having a fourth coefficient of thermal expansion different from the first and second thermal coefficients of expansion. One of the first and second insulating materials has an intrinsic compressive stress, and the other of the first and second insulating materials has an intrinsic tensile stress.

In another example embodiment, a thermal conductivity detector comprises: a principle structure defining a cavity, the principle structure principally comprising a material having a first coefficient of thermal expansion; a sensing element for sensing a thermal conductivity of a gas flowing within the cavity, the sensing element having a second coefficient of thermal expansion different from the first coefficient of thermal expansion, the sensing element being disposed at least in part within the cavity; an insulating structure substantially encasing the sensing element, the insulating structure having a third coefficient of thermal expansion different from the first and second thermal coefficients of expansion, a first end of the insulating structure being attached at a first end of the cavity to a first side to the principle structure defining the cavity; and a compensator disposed at least in part within the cavity, the compensator having a fourth coefficient of thermal expansion different from the first and second coefficients of thermal expansion. The compensator has a first end that is attached to the insulating structure at a second end of the insulating structure opposite the first end thereof, and a second end that is attached at a second end of the cavity opposite the first end thereof to a second side of the principle structure opposite the first side thereof.

In yet another example embodiment, a thermal conductivity detector comprises: a structure defining a cavity, the structure principally comprising a material having a first coefficient of thermal expansion; a sensing element for sensing a thermal conductivity of a gas flowing within the cavity, the sensing element having a second coefficient of thermal expansion different from the third first coefficient of thermal expansion, the filament being disposed at least in part within the cavity; and a compensation structure having a third coefficient of thermal expansion different from the first and second thermal coefficients of expansion. Over a selected temperature range, a stress within the sensing element is less than a yield stress of any component of the sensing element, and a stress within the compensation structure is less than a yield stress of any component of the compensation structure.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIG. 3A illustrates another prior art thermal conductivity detector.

FIG. 3B illustrates a problem with the prior art thermal conductivity detector of FIG. 3a.

FIG. 4 shows a structure for explaining a problem in a prior art thermal conductivity detector.

FIG. 5 illustrates one embodiment of a thermal conductivity detector according to one or more principles disclosed herein.

FIG. 6 illustrates another embodiment of a thermal conductivity detector according to one or more principles disclosed herein.

FIG. 7 illustrates another embodiment of a thermal conductivity detector according to one or more principles disclosed herein.

DETAILED DESCRIPTION

Figure 1:
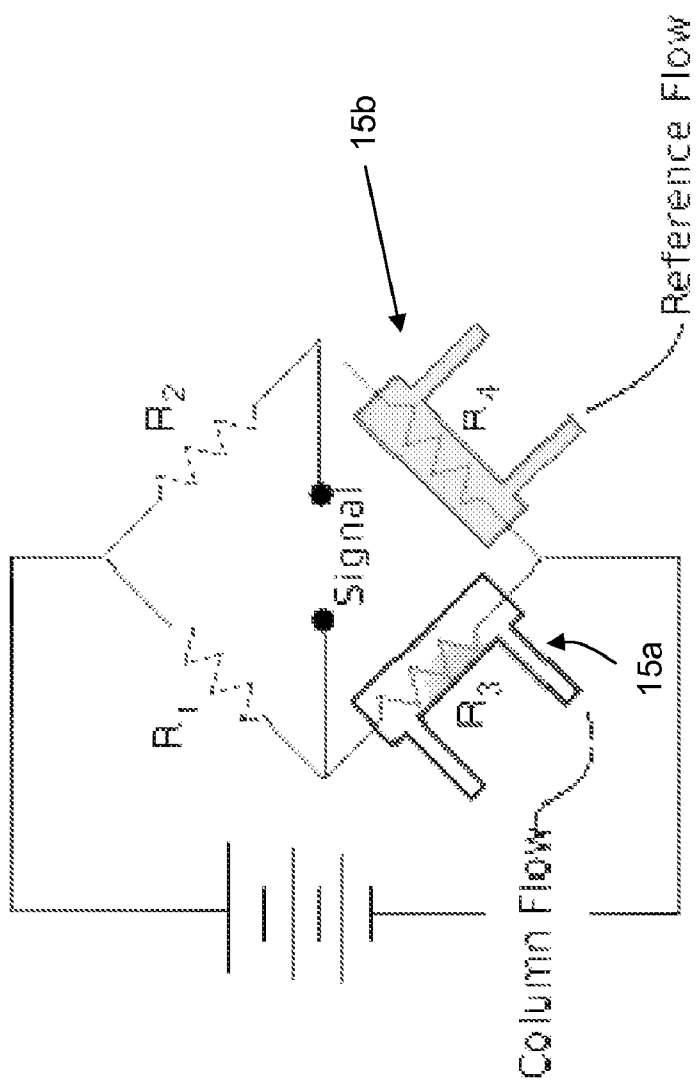
FIG. 1 illustrates a Wheatstone bridge employing thermal conductivity detectors which can be employed in a gas chromatography system.
Figure 2:
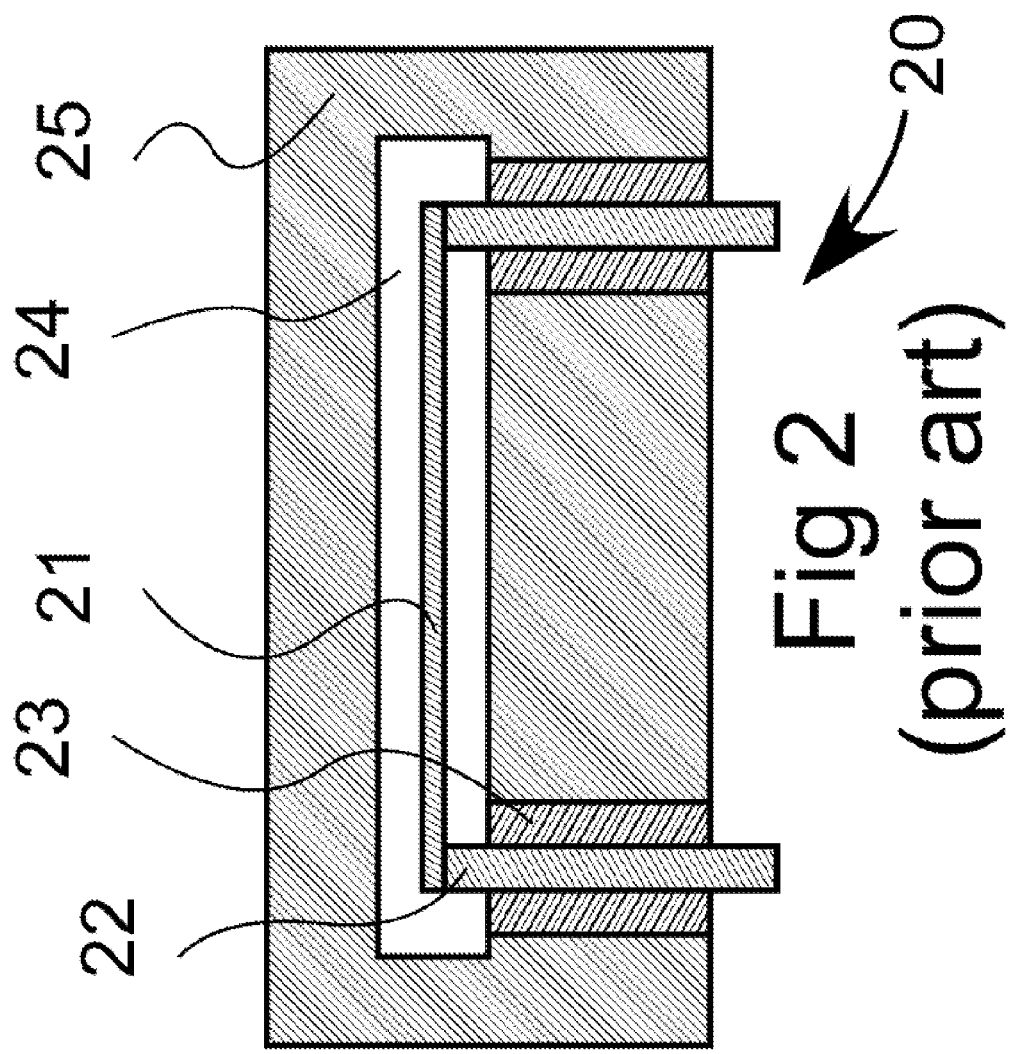
FIG. 2 illustrates a prior art thermal conductivity detector.

In the following detailed description, for purposes of explanation and not limitation, example embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. As used herein, "approximately" means within 10%, and "substantially" means at least 75%. As used herein, when a first structure, material, or layer is said to cover a second structure, material, or layer, this includes cases where the first structure, material, or layer substantially or completely encases or surrounds the second structure, material or layer.

At the outset, it should be understood that intrinsic stress is a property of a thin-film layer deposited on a substrate which is distinct from the coefficient of thermal expansion (CTE) of that layer. As an example, a thin film of hydrogenated silicon nitride (designated as a $Si_xN_yH_z$ film) deposited atop a silicon substrate at 450° C. by means of plasma-enhanced chemical vapor deposition (PECVD) can have a CTE on the order of $3.3 \times 10^{-6}$ per degree Celsius (equal to 3.3 parts per million per degree C., abbreviated as 3.3 ppm/° C.) and can have an intrinsic compressive stress in the range of $2 \times 10^8$ to $6 \times 10^8$ Pascals (200-600 MegaPascals, abbreviated 200-600 MPa) at the deposition temperature. As the silicon substrate cools from the deposition temperature to room temperature, the stress in the deposited film changes due to the difference in CTE between the silicon substrate and the deposited film. Silicon has a CTE which varies with temperature, but by way of example assume that the CTE of silicon is a constant 2.6 ppm/° C. Under this assumption, the $Si_xN_yH_z$ film tends to shrink more than the Si substrate as the temperature falls from 450° C. to a room temperature of 25° C. If there were no intrinsic stress in the $Si_xN_yH_z$ film it would end up in tension at room temperature. However, because intrinsic compressive stress is present, the $Si_xN_yH_z$ film ends up still in compression at room temperature, but with a smaller value of compressive stress than at its deposition temperature.

The simple example above illustrates the types of stresses, and the change in such stresses with temperature, that are encountered in a thin film having a CTE and an intrinsic stress deposited at one temperature on a substrate having a different CTE, which substrate and deposited film then change to a different temperature after the film is deposited.

Likewise, metal films suitable for use as filament materials have their own CTEs and intrinsic stresses, and their interactions with layers such as a $Si_xN_yH_z$ film can be predicted and modeled. For example, it will be appreciated that, if an area of $Si_xN_yH_z$ film as discussed above is first deposited at 450° C. on a silicon substrate, and then an area of tungsten film having a CTE of 4.5 ppm/° C. and an intrinsic stress of zero at room temperature is deposited atop the area of $Si_xN_yH_z$ film, and then a portion of the silicon substrate beneath the area of two films is removed leaving the two films cantilevered from one edge, the result is a bi-layer cantilever tending to curl upward away from the silicon substrate at room temperature due to compressive stress in the $Si_xN_yH_z$ film. It will be further appreciated than as temperature is increased from room temperature, the upward curvature will relax toward flatness at some temperature as the tungsten film expands more than the $Si_xN_yH_z$ film due to its higher CTE. At a high enough temperature, the film will begin to curl downward toward the silicon substrate.

FIG. 4 shows a structure for explaining a problem in a prior art thermal conductivity detector. FIG. 4 illustrates a situation where, first, a $Si_xN_yH_z$ film 42 as discussed above is deposited on a first substrate 41 (e.g., a silicon substrate), and then an area of tungsten thin film 43 as discussed above is deposited atop the $Si_xN_yH_z$ film, and then a second layer of $Si_xN_yH_z$ film 44 is deposited atop the tungsten, and a portion of the substrate 41 is removed to leave a cantilever 45 of $Si_xN_yH_z$, tungsten, and $Si_xN_yH_z$. Finally a second substrate 46 having a second trough is placed over first substrate 41 to define a cavity with the tungsten thin film 43 structure disposed within. It will be appreciated that, if the forces in the two $Si_xN_yH_z$ films 42 and 44 are well balanced around the central tungsten layer 43, that the result can be a composite cantilever 45 which neither curls up nor down, but in which nevertheless tungsten layer 43 having zero intrinsic stress experiences tensile stress due to the presence of compressive stress in the two $Si_xN_yH_z$ films 42 and 44 encasing it.

Figure 3B:
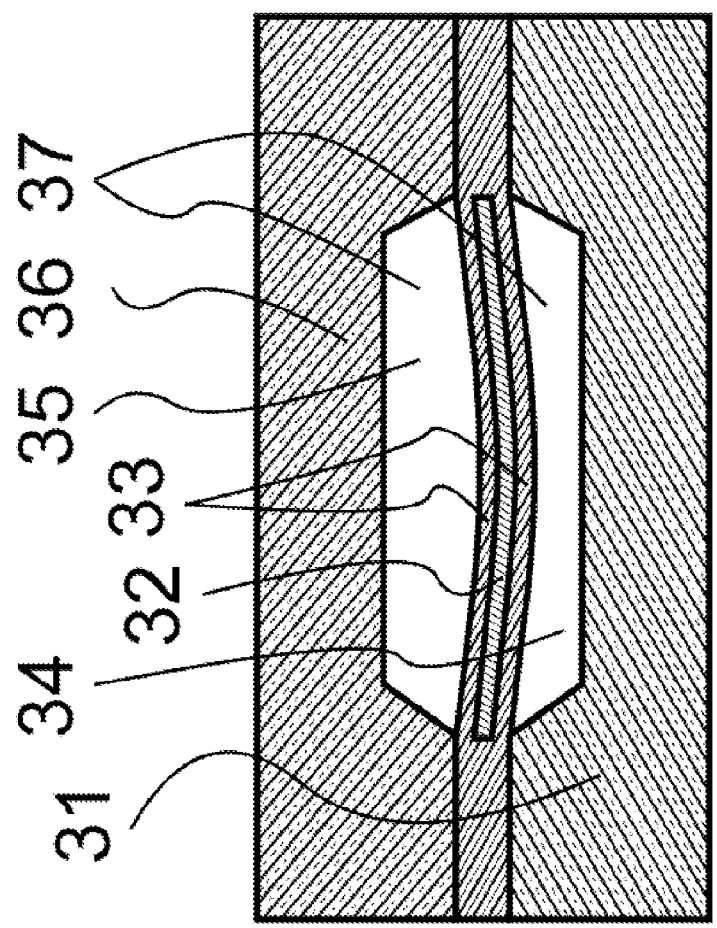

If the free end of composite cantilever 45 was then attached to the substrates 41 and 46 at room temperature to form a doubly-clamped composite beam, as depicted in FIG. 3A above, and the assembly was heated, the overall force in the beam would become compressive and the beam would eventually buckle at some temperature as shown in FIG. 3B. Such a buckling increases the gas thermal conductance across the trough 34 between the filament 32 and the substrate 31, and is spuriously seen as an increase in the thermal conductivity of the gas, so that the device is not useful at this high temperature. Thus it is necessary to prevent buckling of the filament in order to have utility at the high temperature.

Accordingly, when the thermal properties of a thin film material and a substrate are sufficiently compatible, utility over a wide temperature range may be provided. Otherwise, a solution is needed to allow operation over a wide temperature range.

The present inventor has further appreciated that, when the properties of one thin film material and a substrate are not compatible enough to provide utility over a wide temperature range, the addition of one or more additional thin film materials having different thermal properties, the added materials being in intimate contact with the previous materials, may suffice to provide utility over a desired wide temperature range.

FIG. 5 illustrates one embodiment of a thermal conductivity detector (TCD) 50 according to one or more principles disclosed herein.

TCD 50 includes: a first substrate 51; a sensing element 52; an electrically insulating structure 53, a second substrate 56 and a compensator 59 comprising a compensator material 58.

First and second substrates 51 and 56 together form a principle structure of TCD 30, and together define a cavity or channel 57 in which sensing element 52 is, at least in part, disposed, and through which the sample gas whose properties are to be monitored can flow. Cavity 57 includes first and second troughs 54 and 55 with sensing element 52 suspended therebetween such that column effluent comprising a sample gas flows around it, thereby allowing TCD 50 to detect the thermal conductivity of the gas.

First and second substrates 51 and 56 are semiconductor substrates, for example, silicon substrates.

Sensing element 52 comprises a filament formed of a thin resistive film composed of, for example, tungsten or nickel or platinum. Beneficially, sensing element 52 comprises a tungsten thin-film filament having either an intrinsic compressive stress or a near-zero intrinsic stress.

Insulating structure 53 covers sensing element 52. Beneficially, insulating structure 53 substantially encases or surrounds sensing element 52. Insulating structure 53 is beneficially formed of a chemically resistant, electrically insulating thin film. Insulating structure 53 may comprise one of, for example, sputtered pyrex, silicon dioxide, silicon nitride, silicon oxynitride, hydrogenated silicon nitride or silicon-rich silicon nitride. Beneficially insulating structure 53 has an intrinsic compressive stress. Beneficially insulating structure 53 comprises hydrogenated silicon nitride having an intrinsic compressive stress.

Beneficially, compensator material 58 of compensator 59 comprises hydrogenated silicon nitride. Beneficially, compensator material 58 has an intrinsic tensile stress.

One method of fabricating microscale TCD 50 is as follows. A first layer of insulating material (e.g., $Si_xN_yH_z$) for insulating structure 53 is formed (e.g., deposited) on substrate 51. A tungsten thin-film filament for sensing element 52 is formed on the first layer of insulating material. Then another layer of insulating material for insulating structure 53 covers the tungsten thin-film filament 52. Finally, compensator material 58 for compensator 59 is formed on first substrate 51 so as to contact insulating structure 53.

A region of the substrate 51 beneath the structure comprising filament 52, insulating structure 53, and compensator 59 is typically removed by means of chemical etching, leaving filament 52 suspended above a trough 54 formed in substrate 51. The resulting structure includes insulating structure 53 being attached to first substrate 51 at one end of trough 54, compensator 59 being attached to the opposite end of trough 54, and insulating structure 53 being attached to compensator 59, with filament 52, insulating structure 53, and compensator 59 being in a generally co-linear arrangement.

The principle structure of TCD 50 is completed by placing second substrate 56, having a second trough 55 formed therein, atop first substrate 51 whereby the two troughs 54 and 55 form the enclosing cavity or channel 57, along which a column effluent comprising a sample gas can flow around filament 52, insulating structure 53, and compensator 59, thereby allowing TCD 50 to detect the thermal conductivity of the gas.

Beneficially insulating structure 53 and compensator 59 each have a CTE which differs from the CTE of filament 52 and the CTE of the principle structure comprising substrates 51 and 56. However, the CTEs of the materials comprising filament 52, insulating structure 53, and compensator 59 cannot be easily selected to have any desired values. The CTE of filament 52 is typically that of tungsten, platinum, nickel, or some other metal and tends to be substantially higher than CTE of silicon substrates 51 and 56.

The CTE of insulating structure 53 is typically close to that of compensator 59, and both are typically close to that of silicon nitride, and are not easily selectable. Beneficially, the CTE of insulating structure 53 is substantially the same as that of compensator 59. Likewise, the intrinsic stress in insulating structure 53 is typically compressive because compressive silicon nitride formed by plasma-enhanced chemical vapor deposition (PECVD) is denser than tensile PECVD silicon nitride, and so provides superior chemical passivation at high temperature compared to tensile PECVD silicon nitride. However, the characteristics of compensator 59, other than its CTE, are easily selectable over wide ranges consistent with the design goals of preventing buckling or breakage of filament 52. Selectable characteristics of compensator 59 can include intrinsic stress magnitude, thickness, width, and length.

It will be appreciated by those skilled in the art of microscale device fabrication that additional layers may be present in TCD 50 to promote adhesion of layers within the structure, or to provide desired selectivity in etching during the process of fabrication of the structure, or to provide other functionality, and that such additional layers may be present in various configurations without departing from the scope or spirit of the present invention.

FIG. 6 illustrates another embodiment of a thermal conductivity detector 60 according to one or more principles disclosed herein. TCD 60 comprises a first substrate 61, a sensing element 62, an electrically insulating structure 63, compensator regions 68 and 69, and a second substrate 66.

First and second substrates 61 and 66 together form a principle structure of TCD 60, and together define a cavity or channel 67 in which sensing element 62 is, at least in part, disposed, and through which the sample gas whose properties are to be monitored can flow. Cavity 67 includes first and second troughs 64 and 65 with sensing element 62 suspended therebetween such that column effluent comprising a sample gas flows around it, thereby allowing TCD 60 to detect the thermal conductivity of the gas.

First and second substrates 61 and 66 are semiconductor substrates, for example, silicon substrates.

Sensing element 62 comprises a filament formed of a thin resistive film composed of, for example, tungsten or nickel or platinum. Beneficially, sensing element 62 comprises a tungsten thin-film filament having an either an intrinsic compressive stress or a near-zero intrinsic stress.

Electrically insulating structure 63 covers sensing element 62. Beneficially, electrically insulating structure 63 substantially encases or surrounds sensing element 62. Electrically insulating structure 63 is beneficially formed of a first insulating material. Beneficially, the first insulating material comprises a chemically resistant, electrically insulating thin film. The first insulating material for electrically insulating structure 63 may comprise one of, for example, sputtered pyrex, silicon dioxide, silicon nitride, silicon oxynitride, hydrogenated silicon nitride or silicon-rich silicon nitride. Beneficially the electrically insulating material for electrically insulating structure 63 has an intrinsic compressive stress. Beneficially the electrically insulating structure 63 comprises hydrogenated silicon nitride having an intrinsic compressive stress. Beneficially the first insulating material for electrically insulating structure 63 has a CTE which differs from the CTE of filament 62 and the principle structure comprising substrates 61 and 66.

Compensator regions 68 and 69 comprise a compensator for TCD 60. Beneficially, compensator regions 68 and 69 comprise a second insulating material, beneficially, hydrogenated silicon nitride. Beneficially, the second insulating material of compensator regions 68 and 69 has an intrinsic tensile stress, and therefore performs a compensation function with respect to filament 62 and electrically insulating structure 63. Beneficially the second insulating material of compensator regions 68 and 69 has a CTE which differs from the CTE of filament 62 and the principle structure comprising substrates 61 and 66. Beneficially, the CTE of the second insulating material is substantially the same as that of the first insulating material of electrically insulating structure 63.

One method of fabricating microscale TCD 60 is as follows. A first layer of second insulating material (e.g., $Si_xN_yH_z$) for compensator region 69 is formed (e.g., deposited) on substrate 61. Then a first layer of first insulating material (e.g., $Si_xN_yH_z$) for electrically insulating structure 63 is formed (e.g., deposited) on the first layer of second insulating material of compensator region 69. A tungsten thin-film filament for sensing element 62 is formed on the first layer of first insulating material of electrically insulating structure 63. Then another layer of first insulating material (e.g., $Si_xN_yH_z$) for electrically insulating structure 63 covers the sensing element 62. Finally, a second layer of second insulating material (e.g., $Si_xN_yH_z$) for compensator region 68 is formed (e.g., deposited) on electrically insulating structure 63.

A region of the substrate 61 beneath the structure comprising filament 62, electrically insulating structure 63, and compensator regions 68 and 69 is typically removed by means of chemical etching, leaving filament 62 suspended above a trough 64 formed in substrate 61.

The principle structure of TCD 60 is completed by placing second substrate 66 having a second trough 65 formed therein atop first substrate 61 whereby the two troughs 64 and 65 form the enclosing cavity or channel 67, along which a column effluent comprising a sample gas can flow around filament 62, electrically insulating structure 63, and compensator regions 68 and 69, thereby allowing TCD 60 to detect the thermal conductivity of the gas.

It will be appreciated by those skilled in the art of microscale device fabrication that additional layers may be present in TCD 50 to promote adhesion of layers within the structure, or to provide desired selectivity in etching during the process of fabrication of the structure, or to provide other functionality, and that such additional layers may be present in various configurations without departing from the scope or spirit of the present invention.

It will be appreciated that there is less design freedom in designing TCD 60 than in designing TCD 50. In TCD 60, the lengths of compensator regions 68 and 69 are generally constrained to be the same as the length of electrically insulating structure 63, while in TCD 50 the length of compensator 59 may be different than the length of insulating structure 53. However, TCD 60 may be more compact than TCD 50.

FIG. 7 illustrates another embodiment of a thermal conductivity detector 70 according to one or more principles disclosed herein. TCD 70 comprises a first substrate 71; a sensing element 72; a first electrically insulating structure 73, a second electrically insulating structure 78, a compensator structure 79, and a second substrate 76.

First and second substrates 71 and 76 together form a principle structure of TCD 70, and together define a cavity or channel 77 in which sensing element 72 is, at least in part, disposed, and through which the sample gas whose properties are to be monitored can flow. Cavity 77 includes first and second troughs 74 and 75 with sensing element 72 suspended therebetween such that column effluent comprising a sample gas flows around it, thereby allowing TCD 70 to detect the thermal conductivity of the gas.

First and second substrates 71 and 76 are semiconductor substrates, for example, silicon substrates.

Beneficially, sensing element 72 comprises a filament formed of a thin resistive film composed of, for example, tungsten or nickel or platinum. Beneficially, sensing element 72 comprises a tungsten thin-film filament having near-zero intrinsic stress.

First electrically insulating structure 73 substantially is disposed beneath sensing element 72. First electrically insulating structure 73 is beneficially formed of a first insulating material. Beneficially, the first insulating material comprises a chemically resistant, electrically insulating thin film. The first insulating material of first electrically insulating structure 73 may comprise one of, for example, sputtered pyrex, silicon dioxide, silicon nitride, silicon oxynitride, hydrogenated silicon nitride or silicon-rich silicon nitride. Beneficially the first insulating material for first electrically insulating structure 73 has an intrinsic tensile stress. Beneficially first electrically insulating structure 73 comprises silicon-rich silicon nitride having an intrinsic tensile stress. Beneficially the first insulating material of first electrically insulating structure 73 has a CTE which differs from the CTE of filament 72 and the principle structure comprising substrates 71 and 76.

Second electrically insulating structure 78 substantially is disposed atop sensing element 72. Second electrically insulating structure 78 is beneficially formed of a second insulating material. Beneficially, the second insulating material comprises a chemically resistant, electrically insulating thin film. The second insulating material of second electrically insulating structure 78 may comprise one of, for example, sputtered pyrex, silicon dioxide, silicon nitride, silicon oxynitride, hydrogenated silicon nitride or silicon-rich silicon nitride. Beneficially the electrically insulating material of second electrically insulating structure 78 has an intrinsic compressive stress. Beneficially second electrically insulating structure 78 comprises hydrogenated silicon nitride having an intrinsic compressive stress. Beneficially the second insulating material of second electrically insulating structure 78 has a CTE which differs from the CTE of filament 72 and the principle structure comprising substrates 71 and 76.

Compensator structure 79 comprises a compensator for TCD 70. Beneficially, compensator structure 79 comprises a third insulating material, beneficially, hydrogenated silicon nitride. Beneficially, the third insulating material of compensator structure 79 has an intrinsic tensile stress, and therefore performs a compensation function with respect to filament 72, first electrically insulating structure 73, and second insulating structure 78, thereby providing a materials stack 80 which displays minimal tendency to bend or curl during excursions in temperature. Beneficially the third insulating material of compensator structure 79 has a CTE which differs from the CTE of filament 72 and the principle structure comprising substrates 71 and 76. Beneficially, the CTEs of the first, second, and third insulating materials are substantially equal.

One method of fabricating microscale TCD 70 is as follows. A first layer of first insulating material (e.g., $Si_xN_y$) for first electrically insulating structure 73 is formed (e.g., deposited) on substrate 71. A tungsten thin-film filament for sensing element 72 is formed on the first insulating material of first electrically insulating structure 73. Then, a layer of second insulating material e.g., $Si_xN_yFi_z$) for second insulating structure 78 covers the tungsten thin-film filament 72 and, beneficially, the first layer of first insulating material of first electrically insulating structure 73. Finally, a layer of third insulating material (e.g., $Si_xN_yFi_z$) for compensator structure 79 is formed (e.g., deposited) on the layer of second insulating material of second electrically insulating structure 78.

A region of the substrate 71 beneath the materials stack 80 is typically removed by means of chemical etching, leaving filament 72 suspended above a trough 74 formed in substrate 71.

The principle structure of TCD 70 is completed by placing second substrate 76 having a second trough 75 formed therein atop first substrate 71 whereby the two troughs 74 and 75 form the enclosing cavity or channel 77, along which a column effluent comprising a sample gas can flow around filament 72, first electrically insulating structure 73, second electrically insulating structure 78, and compensator structure 79, thereby allowing TCD 70 to detect the thermal conductivity of the gas.

It will be appreciated by those skilled in the art of microscale device fabrication that additional layers may be present in TCD 70 to promote adhesion of layers within the structure, or to provide desired selectivity in etching during the process of fabrication of the structure, or to provide other functionality, and that such additional layers may be present in various configurations without departing from the scope or spirit of the present invention.

It will be appreciated that there is less design freedom in designing TCD 70 than in designing TCD 50. However, TCD 70 may be more compact than TCD 50.

While example embodiments are disclosed herein, one of ordinary skill in the art appreciates that many variations that are in accordance with the present teachings are possible and remain within the scope of the appended claims. The invention therefore is not to be restricted except within the scope of the appended claims.

The invention claimed is:

1. A thermal conductivity detector, comprising:
   a structure defining a cavity, the structure principally comprising a material having a first coefficient of thermal expansion;
   a sensing element for sensing a thermal conductivity of a gas flowing within the cavity, the sensing element having a second coefficient of thermal expansion different from the first coefficient of thermal expansion, the sensing element being disposed at least in part within the cavity;
   a first insulating material substantially covering the sensing element, the first insulating material having a third coefficient of thermal expansion different from the first and second thermal coefficients of expansion; and
   a second insulating material substantially covering the first insulating material, the second insulating material having a fourth coefficient of thermal expansion different from the first and second thermal coefficients of expansion,
   wherein one of the first and second insulating materials has an intrinsic compressive stress, and the other of the first and second insulating materials has an intrinsic tensile stress.

2. The thermal conductivity detector of claim 1, wherein the structure comprises a first semiconductor substrate, and a second semiconductor substrate disposed on the first semiconductor substrate.

3. The thermal conductivity detector of claim 2, wherein the first and second insulating materials are provided on a top surface of the first semiconductor substrate, and wherein a bottom surface of the second semiconductor substrate is disposed on the first and second insulating materials.

4. The thermal conductivity detector of claim 1, wherein the sensing element is a metal filament.

5. The thermal conductivity detector of claim 1, wherein the metal filament is one of nickel, tungsten and platinum.

6. The thermal conductivity detector of claim 1, wherein the first insulating layer comprises a hydrogenated silicon nitride.

7. The thermal conductivity detector of claim 6, wherein the second insulating layer comprises a hydrogenated silicon nitride.

8. The thermal conductivity detector of claim 1, wherein the third and fourth thermal coefficients of expansion are substantially the same.

9. The thermal conductivity detector of claim 1, further comprising a third insulating material substantially disposed beneath the sensing element, on an opposite side of the sensing element as the first insulating material, the third insulating material having a coefficient of thermal expansion different from the first and second thermal coefficients of expansion.

10. A thermal conductivity detector, comprising:
    a principle structure defining a cavity, the principle structure principally comprising a material having a first coefficient of thermal expansion;
    a sensing element for sensing a thermal conductivity of a gas flowing within the cavity, the sensing element having a second coefficient of thermal expansion different from the first coefficient of thermal expansion, the sensing element being disposed at least in part within the cavity;

an insulating structure substantially encasing the sensing element, the insulating structure having a third coefficient of thermal expansion different from the first and second thermal coefficients of expansion, a first end of the insulating structure being attached at a first end of the cavity to a first side to the principle structure defining the cavity; and a compensator disposed at least in part within the cavity, the compensator having a fourth coefficient of thermal expansion different from the first and second thermal coefficients of expansion, wherein the compensator includes:

a first end that is attached to the insulating structure at a second end of the insulating structure opposite the first end thereof, and a second end that is attached at a second end of the cavity opposite the first end thereof to a second side of the principle structure opposite the first side thereof.

11. The thermal conductivity detector of claim 10, wherein the principle structure comprises a first semiconductor substrate, and a second semiconductor substrate disposed on the first semiconductor substrate.

12. The thermal conductivity detector of claim 11, wherein the insulating structure is provided on a top surface of the first semiconductor substrate, and wherein a bottom surface of the second semiconductor substrate is disposed on the insulating material at the first side of the principle structure, and wherein the compensator is provided on a top surface of the first semiconductor substrate, and wherein a bottom surface of the second semiconductor substrate is disposed on the compensator at the second side of the principle structure.

13. The thermal conductivity detector of claim 10, wherein the sensing element is a metal filament.

14. The thermal conductivity detector of claim 13, wherein the metal filament is one of nickel, tungsten and platinum.

15. The thermal conductivity detector of claim 10, wherein one of the insulating structure and the compensator has an intrinsic compressive stress, and the other of the insulating structure and the compensator has an intrinsic tensile stress.

16. The thermal conductivity detector of claim 10, wherein the third and fourth thermal coefficients of expansion are substantially the same.

17. A thermal conductivity detector, comprising:

a structure defining a cavity, the structure principally comprising a material having a first coefficient of thermal expansion;

a sensing element for sensing a thermal conductivity of a gas flowing within the cavity, the sensing element having a second coefficient of thermal expansion different from the third coefficient of thermal expansion, the sensing element being disposed at least in part within the cavity; and a compensation structure adapted to compensate for a difference between the first and second thermal coefficients of expansion, wherein over a selected temperature range, a stress within the sensing element is less than a yield stress of any component of the sensing element, and a stress within the compensation structure is less than a yield stress of any component of the compensation structure, and wherein the selected temperature range is at least between 0° C. and 400° C.

18. The thermal conductivity detector of claim 17, wherein the sensing element is a metal filament.

19. The thermal conductivity detector of claim 17, wherein the compensation structure comprises:

a first insulating material substantially covering the sensing element, the first insulating material having a third coefficient of thermal expansion different from the first and second thermal coefficients of expansion; and a second insulating material substantially covering the first insulating material, the second insulating material having a fourth coefficient of thermal expansion different from the first and second thermal coefficients of expansion.

20. The thermal conductivity detector of claim 17, further comprising an insulating structure substantially encasing the sensing element, the insulating structure having a third coefficient of thermal expansion different from the first and second thermal coefficients of expansion, a first end of the insulating structure being attached at a first end of the cavity to a first side to the principle structure defining the cavity, wherein the compensation structure is disposed at least in part within the cavity, the compensation structure having a fourth coefficient of thermal expansion different from the first and second thermal coefficients of expansion, and wherein the compensation structure includes:

a first end that is attached to the insulating structure at a second end of the insulating structure opposite the first end thereof, and a second end that is attached at a second end of the cavity opposite the first end thereof to a second side of the principle structure opposite the first side thereof.

* * * * *

UNITED STATES PATENT AND TRADEMARK OFFICE
CERTIFICATE OF CORRECTION

PATENT NO. : 8,313,236 B2
APPLICATION NO. : 12/613670
DATED : November 20, 2012
INVENTOR(S) : Phillip W. Barth It is certified that error appears in the above-identified patent and that said Letters Patent is hereby corrected as shown below:

In column 12, line 4, in Claim 17, delete "third" and insert -- first --, therefor.

Signed and Sealed this
Second Day of April, 2013

Teresa Stanek Rea
*Acting Director of the United States Patent and Trademark Office*